United States Patent
Smyth

(10) Patent No.: US 6,687,332 B2
(45) Date of Patent: Feb. 3, 2004

(54) METHOD AND APPARATUS FOR PATIENT-IN-PLACE MEASUREMENT AND REAL-TIME CONTROL OF BEAM-SPOT POSITION AND SHAPE IN A SCANNING ELECTRON BEAM COMPUTED TOMOGRAPHIC SYSTEM

(75) Inventor: Brian Smyth, San Francisco, CA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 194 days.

(21) Appl. No.: 10/094,543

(22) Filed: Mar. 8, 2002

(65) Prior Publication Data

US 2003/0169849 A1 Sep. 11, 2003

(51) Int. Cl.$^7$ .................................................. H05G 1/52
(52) U.S. Cl. .......................... 378/113; 378/137; 378/4; 378/10; 378/19
(58) Field of Search .................................. 378/137, 113, 378/19, 12, 10, 138, 147, 4, 14; 250/396; 313/424

(56) References Cited

U.S. PATENT DOCUMENTS

| | | | |
|---|---|---|---|
| 4,352,021 A | 9/1982 | Boyd et al. ................... 378/12 |
| 4,521,900 A | 6/1985 | Rand ........................... 378/137 |
| 4,631,741 A | 12/1986 | Rand et al. .................... 378/10 |
| 5,212,737 A | * 5/1993 | Ackelsberg ................. 382/131 |
| 5,224,137 A | 6/1993 | Plomgren et al. ............. 378/10 |
| 5,491,734 A | * 2/1996 | Boyd et al. ................... 378/10 |
| 6,130,929 A | * 10/2000 | Saha .............................. 378/4 |

* cited by examiner

Primary Examiner—Craig E. Church
Assistant Examiner—Irakli Kiknadze
(74) Attorney, Agent, or Firm—McAndrews, Held & Malloy, Ltd.; Peter J. Vogel; Michael A. Dellapenna

(57) ABSTRACT

A scanning electron beam computed tomographic system is provided with a sub-collimation system that passes X-rays emitted by a beam spot formed by an electron beam that is scanned across an X-ray emitting target, which X-rays would not otherwise reach an object under X-ray examination with the system. The sub-collimation system includes phantom-like objects that cause X-rays to be blocked, or passed, through to X-ray detectors depending primarily upon the beam spot position and, secondarily, on the beam-spot shape. Detector output signals may be used in real-time to control at least one characteristic of the electron beam-spot in a closed-loop correction system.

21 Claims, 5 Drawing Sheets

METHOD AND APPARATUS FOR PATIENT-IN-PLACE MEASUREMENT AND REAL-TIME CONTROL OF BEAM-SPOT POSITION AND SHAPE IN A SCANNING ELECTRON BEAM COMPUTED TOMOGRAPHIC SYSTEM

FIELD OF THE INVENTION

The present invention relates generally to scanning electron beam systems for X-ray production in a computed tomography X-ray transmission system, and more particularly to reliably controlling the shape and position of an electron beam-spot as it is scanned across target to produce X-rays in such systems.

BACKGROUND OF THE INVENTION

A century ago, mathematician J. Radon demonstrated that a two-dimensional slice of a three-dimensional object may be reproduced from the set of all of its projections. Computed tomography (CT) X-ray systems generate a set of X-ray beam projections through an object to be examined. The resultant detected X-ray data are computer processed to reconstruct a tomographic image-slice of the object.

Conventional CT systems subject the object under examination to one or more pencil-like X-ray beams from all possible directions in a plane. The X-ray data may be generated in fan beam format (as is the case for the present invention), or in parallel beam format. In a fan beam system, the X-rays radiate from a source and are collected in a fan. By contrast, in a parallel beam system the X-rays are all parallel within a view. In either system, a view is one projection of the object onto the detectors, and a scan is a collection of all of the views.

In a fan beam scanning electron beam system such as described in U.S. Pat. No. 4,521,900 to Rand, or U.S. Pat. No. 4,352,021 to Boyd, an electron beam is produced by an electron gun and is accelerated downstream along the z-axis of an evacuated chamber. Further downstream a beam optical system deflects the electron beam about 30° into a scanning path, with azimuthal range typically about 210°. The deflected beam is then focused upon a suitable target, typically a large arc of tungsten material, which produces a fan beam of X-rays.

The emitted X-rays penetrate an object (e.g., a patient) that is disposed along the z-axis and lying, typically upon a couch, within a so-called reconstruction circle. X-ray beams passing through the object are attenuated by various amounts, depending upon the nature of the object traversed (e.g., bone, tissue, metal). One or more X-ray detectors, disposed on the far side of the object, receive these beams and provide signals proportional to the strength of the incoming X-rays. A collimation system is typically disposed between the X-ray detectors and the X-ray target (or targets).

Typically the output data from the detectors are processed using a filtered back-projection algorithm. Detector data representing the object scanned from many directions are arranged to produce image profiles for each scan direction. Since the X-rayed object is not homogeneous, these profiles will vary in intensity with the amount of radiation detected by the various detectors on the various scans. The convoluted data from the various projections are then superimposed, or back-projected, to produce a computed tomographic image of the original object. The thus processed data are used to produce a reconstructed image of a slice of the object, which image may be displayed on a video monitor.

Systems similar to what is described in the above patents to Rand or Boyd are manufactured by Imatron, Inc., located in South San Francisco, Calif. These systems are termed "short scan" because the views used for reconstructing an object image cover 180° plus the fan beam angle (about 30°), e.g., about 210° total, rather than a full 360°. In a scanning electron beam CT system, the 210° angle implies that the target and detector must overlap, which is to say occupy the same space azimuthally.

The quality of the reconstructed image produced by a CT system is highly influenced by the position (measured in time and in radius) and by the shape of the electron-beam spot as it is scanned along the arc-shaped X-ray emitting target. Prior art techniques that attempt to monitor the position and shape of the preferably eclipitically-shaped electron-beam spot are known. U.S. Pat. No. 4,631,741 to Rand and U.S. Pat. No. 5,224,137 to Plomgren, each of which is incorporated herein by reference, disclosed beam-spot monitoring systems in which devices such as "W"-shaped and "Z"-shaped wires were disposed on a target within the vacuum chamber housing, near but separate from the actual X-ray producing arc-like target. These devices produced beam-spot timing and beam elliptical radius data that could provide some indication as to the quality of the beam-spot along the actual arc-like target.

Unfortunately, because the Rand-Plomgren type devices were on a separate target, the data they provided was available only during a calibration step after the beam scan was completed. Thus, data were not provided from these devices in real-time during the actual scan, and would not be available, for example, with a patient-in-position upon the couch. At best, electron beam-spot shape could only be inferred for the actual X-ray emitting arc-like target from data provided by the phantom-like Rand-Plomgren devices. Further, obtaining meaningful information from these devices required operator intervention and calibration that required halting operation of the scanning system, and was therefore performed typically only on a weekly basis. Understandably, since the "W" or "Z"-shaped wire devices were inside the scanner system vacuum chamber housing, accessing these devices for maintenance and calibration was time consuming.

In summary, for use with electron beam scanner systems there is a need for a method and apparatus to monitor in real-time at least electron beam-spot position and preferably also beam shape during actual acquisition of data with a patient-in-place, preferably with a refresh or update rate exceeding once per ms. Preferably such method and apparatus should utilize much of the configuration already in place for an electron beam CT system and should not require generation of additional X-ray beams. Such apparatus should preferably be readily maintainable and should not interfere with normal operation of the electron beam scanner system.

The present invention provides such a method and apparatus.

SUMMARY OF THE INVENTION

In a typical electron beam computed tomography scanner system, the collimation process actually discards the vast majority of generated X-rays. The present invention recognizes that some of the normally discarded X-rays could be used to provide real-time information as to one or more characteristics of the electron beam-spot, such as the position and shape and timing of the electron beam-spot as it is scanned along the source X-ray emitting target, even with a patient-in-place. Advantageously, such X-rays may be collected and used without interfering with normal operation of the CT system.

The CT system is slightly modified to include an extra collimation system. The extra collimation system preferably includes a series of phantom-like objects disposed between the X-ray emitting target and separate detectors disposed to receive at least some of the waste or discarded X-rays not used to acquire an image of the object or patient under X-ray examination. The system of separate detectors is referred to herein as the shielded detector system, e.g., the system is shielded by the collimation system, and it is not necessarily the same detector system that detects X-rays that pass through the object or patient under X-ray examination.

Preferably, construction of the detectors and the phantom-like objects permits gathering information as to beam-spot position (i.e., timing and radius) and preferably also the beam-spot shape, as X-rays are blocked or not blocked from reaching the detectors by the phantom-like objects. As the beam-spot scans along the X-ray producing target, this beam-spot characteristic information may be imparted to multiple detectors substantially simultaneously. This capability can enhance the nature and quality of the information, and provide additional information due to the different apparent angles at which the detectors receive the X-rays. Without limitation, such additional information can include position of the X-ray emitting target. Density of the phantom-like objects is such that there are several objects per detector, which permits obtaining several timing measurements per detector, with a preferably sub-ms overall measurement rate.

The computer system controlling operation of the scanning beam computed tomographic system uses the beam timing, radius, and target position data to make real-time corrections to the electron beam-spot in closed-loop feedback fashion. In this fashion, quality of the computed tomographic image of the patient or object under X-ray examination may be improved, and prior art electron beam-spot sensing devices such as "W"-shaped wires may be dispensed with.

Other features and advantages of the invention will appear from the following description in which the preferred embodiments have been set forth in detail in conjunction with the accompanying drawings.

DESCRIPTION OF THE PREFERRED EMBODIMENTS

Figure 1:
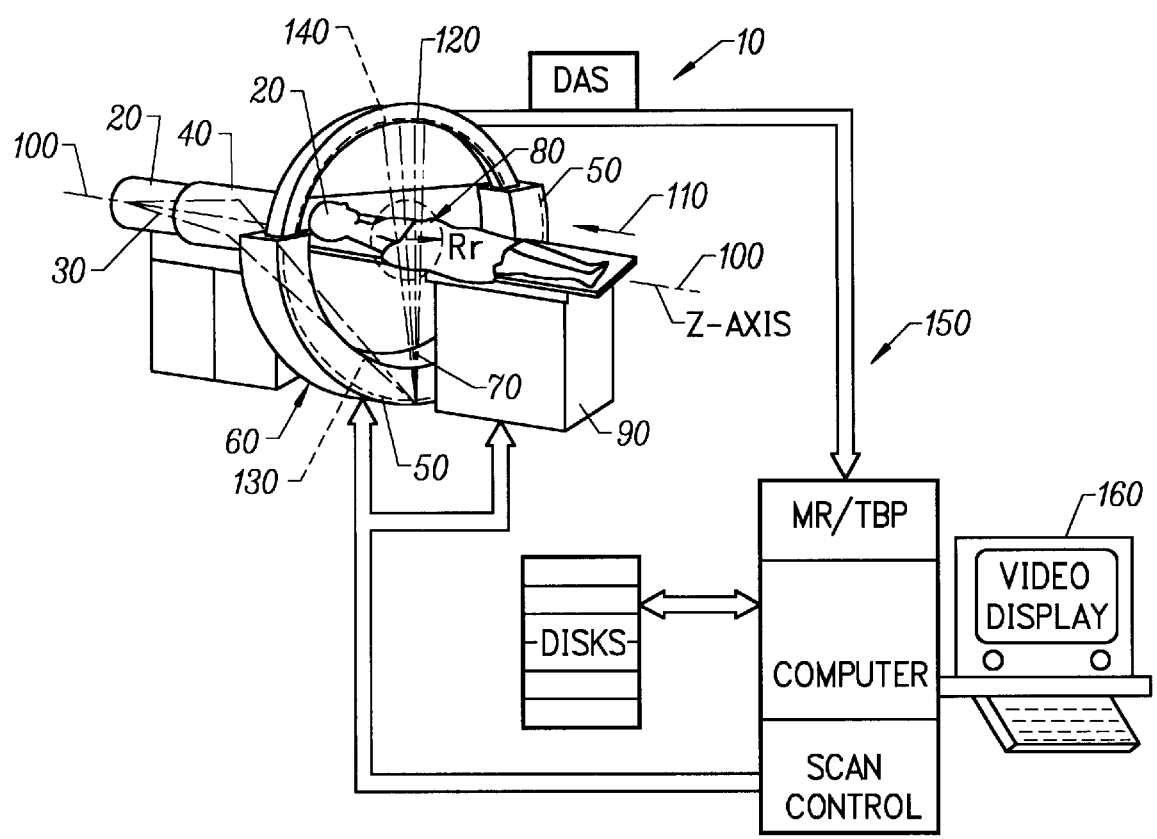
FIG. 1 depicts a scanning electron beam computed tomography X-ray system, according to the present invention.
Figure 2:
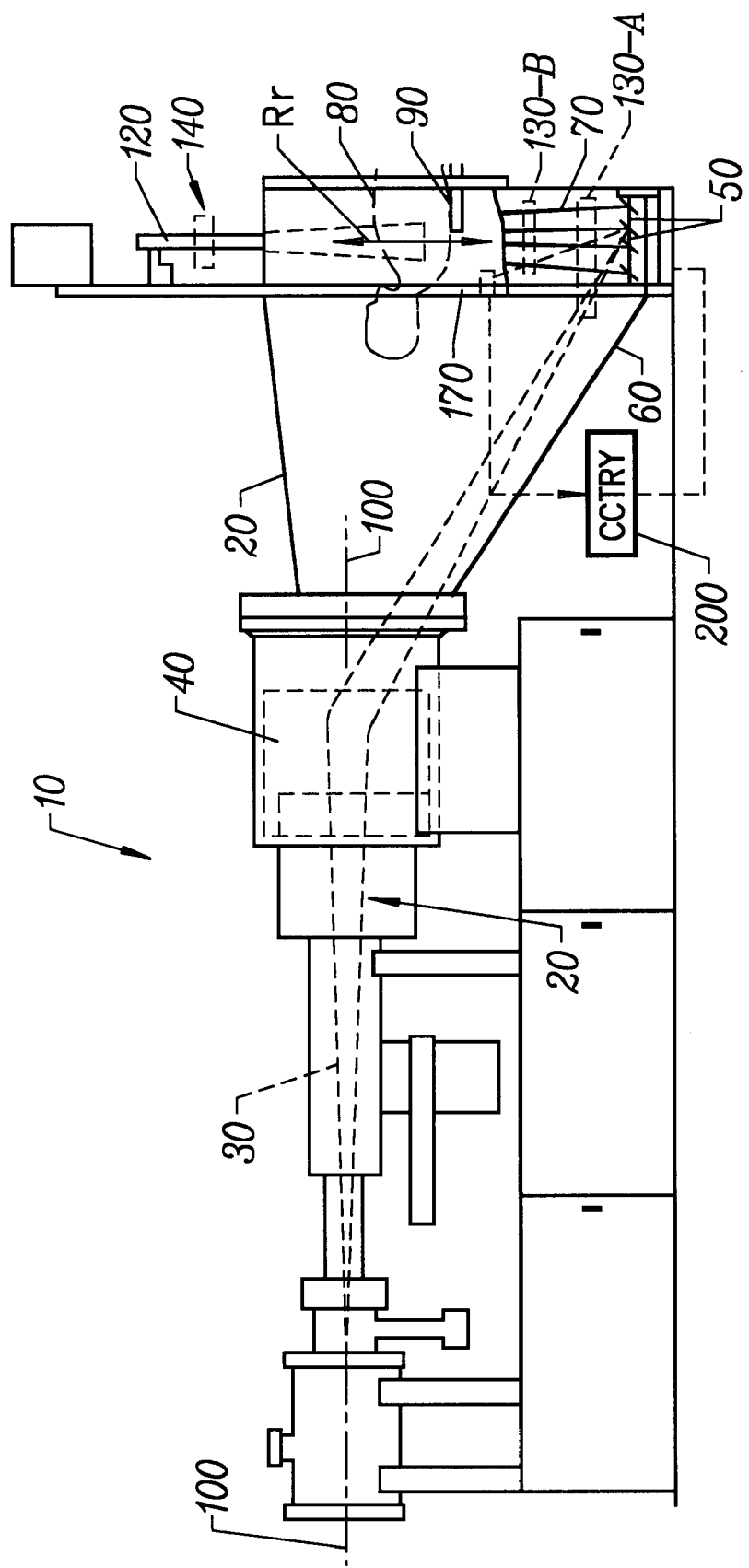
FIG. 2 is a longitudinal view of the system shown in FIG. 1.

FIGS. 1 and 2 depict a scanning electron beam computed tomography (CT) system 10 according to the present invention. System 10 includes a vacuum housing chamber 20 wherein an electron beam 30 is generated and caused by a beam optics assembly 40 to scan at least one circular or arc-like target 50 located within chamber 20's front lower portion 60. Upon being struck by the electron beam, which typically scans 210° or so, target 50 emits a moving fan-like beam of X-rays 70 that pass through a region of a subject 80 (e.g., a patient or other object) within a so-called reconstruction radius Rr. Patient or object 80 typically lies on a couch 90 that is movable along the system z-axis 100 at a chosen velocity, as indicated by arrow 110. X-rays 70 register upon a region of a detector array 120 located generally diametrically opposite the X-ray emitting target 50. System 10 typically includes a lower collimator system 130 that includes collimator elements X-ray pre-collimators 130-A and pre-patient collimators 130-B, generally adjacent target 50, and upper collimator elements 140 with aperture openings 140-A, adjacent detector array 120. The detector array outputs data to a computer processing system 150 that processes and records the data to produce an image of a slice of the subject 80 on a video monitor 160. Computer system 150 can also control operation of system 10, including moving couch 90 along z-axis 100 at a desired velocity. In the present invention, computer system 150 is provided with real-time information with which at least one and preferably several characteristics of the electron beam-spot formed on target 50 may be controlled.

Figure 3:
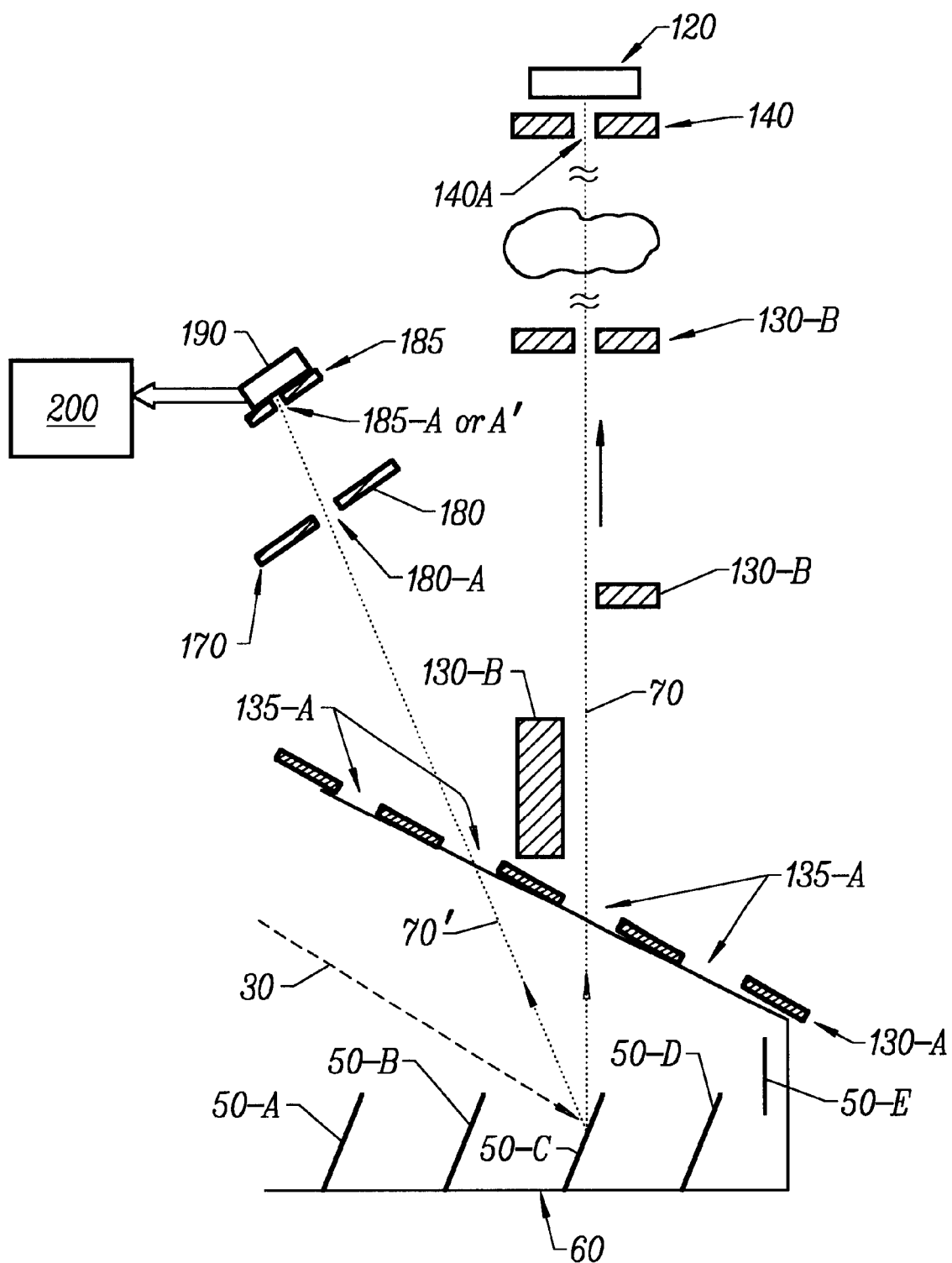
FIG. 3 is a simplified side view showing generation and use of so-called wasted X-ray radiation and a shielded detector array, according to the present invention.

As shown in FIG. 2 and as best seen in FIG. 3, the present invention includes a collimation sub-system 170 and associated circuitry 200. Sub-system 170 preferably includes an X-ray opaque shield 180 that defines apertures 180-A, behind which are located detectors 190 (see also FIG. 4). Collectively, shield 180 and apertures 180-A comprise a series of phantom-like objects. Except for apertures 180-A, detectors 190 are shielded by shield 180 and, accordingly, these detectors will be referred to herein as the shielded detector array. Electronic circuitry 200 receives data from the shielded detector array 190 and processes the data under supervision of computer system 150 to help control the quality of the electron beam-spot upon one or more targets 50.

In the simplified side view of FIG. 3, four X-ray emitting targets 50 are shown, e.g., 50-A, 50-B, . . . along with 50-E, which emits no useable X-rays. As the incoming electron beam 30 is scanned along a target, for example target 50-C in FIG. 3, some of the emitted X-ray energy 70 will be radiated from the target generally in the direction of the object 80 under examination. Pre-colliminator system 130-A comprising X-ray opaque material with openings 135-A and collimators 130-B collimate X-ray radiation 70 toward object 80.

But most X-rays emitted as the electron beam 30 is scanned along target 50-C (or another of the targets) are wasted in the sense that such rays are directed away from the above-noted collimators, and will not strike and perhaps pass at least partially through object 80, and be detected by detector array 120. According to the present invention, at least a portion of such wasted X-rays, indicated by ray 70' in FIG. 3, is caused to pass through sub-system 170, which is to say, the shielded detector array 190, which includes X-ray opaque shield 180 with a plurality of apertures 180-A formed therein. Shielded X-ray detector array 190 is positioned to respond only to X-rays such as 70' that pass through the openings 180-A. Detector signals from detectors such as 190 are coupled to electronic circuit 200 and in a closed-loop feedback configuration help improve the timing and/or radius and/or shape characteristics of the electron beam-spot as the beam-spot is moved along target 50-C (or the other X-ray emitting targets shown in FIG. 3).

Collection and processing of the so-called wasted X-rays occurs in real-time and does not interfere with normal operation of system 10, e.g., the X-ray examination of patient or object 80. Electronic circuitry 200 will extract beam-spot position and preferably beam-spot shape as well from the signals output by detectors 190. When using phantom-like objects and detector shapes as described below, the extraction of such information could be similar to the methods described by Rand and by Plomgren in U.S. Pat. Nos. 4,631,741 and 5,224,137. For example, circuit 200 might implement such methods and algorithms using analog circuitry, digital circuitry, computer-based processing methods, or some combination thereof.

Figure 4:
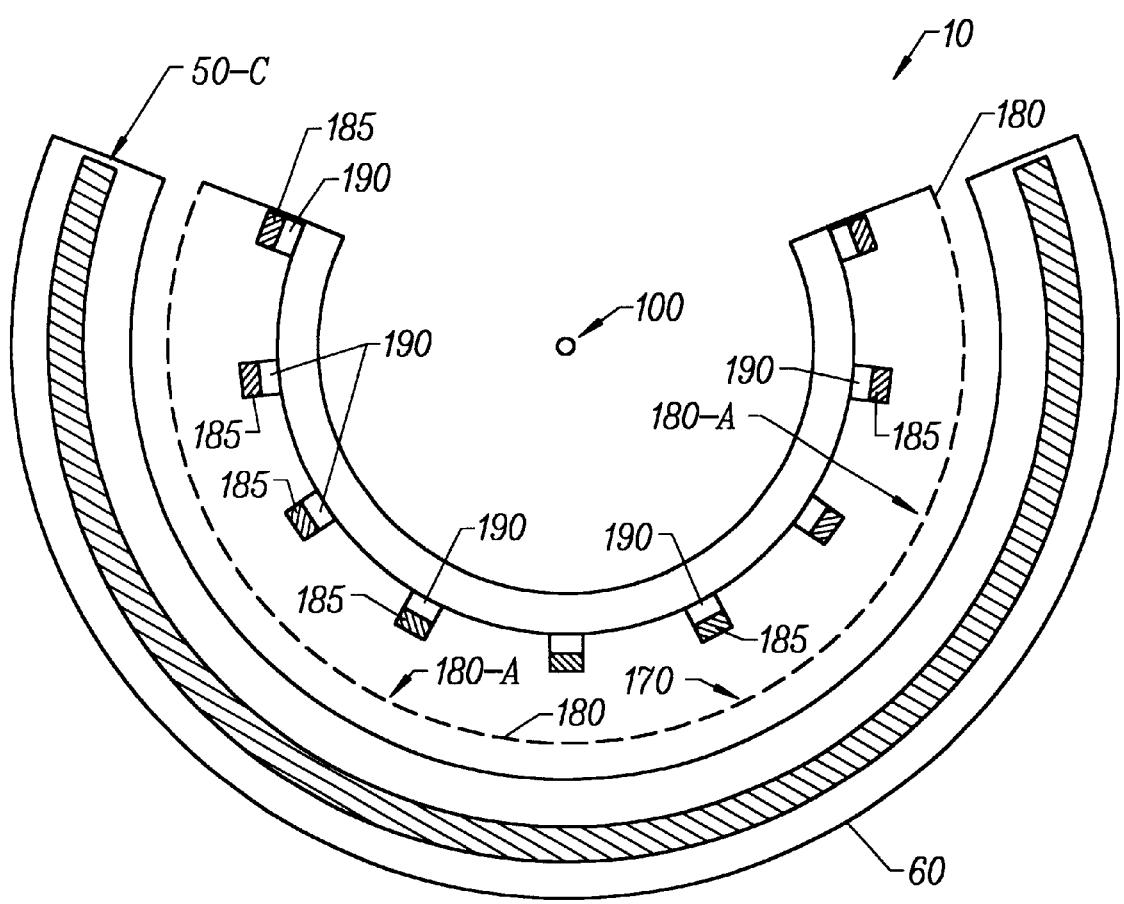
FIG. 4 is a cross-section of a CT scanner system including the present invention, looking from front-to-back or right-to-left in FIGS. 2 and 3, depicting a shielded detector array, according to the present invention.

FIG. 4 is a cross-section of a system 10, for example the C-150 system manufactured by assignee Imatron, Inc. of South San Francisco, Calif., showing a preferred implementation of the shielded detector array as used in the present invention. As seen, in the preferred embodiment, collimation sub-system 170 includes a curved plate of X-ray opaque material 180 in which are defined preferably pinhole-shaped apertures 180-A. It is noted that X-ray emitting target, here target 50-C, plate 170 with apertures 180-A, and detectors 190 are coaxial about the Z-axis 100 of system 10. As the beam-spot moves along a target, X-rays are generated, and some X-rays, e.g., X-rays 70', will pass through the pinhole apertures 180-A. Such passage results in a projection of the beam-spot that moves laterally across the shielded detector 190.

Figure 5A:
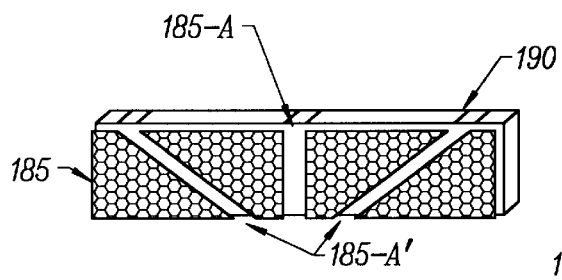
FIG. 5A depicts a "W"-mask shaped aperture mask, according to the present invention.
Figure 5C:
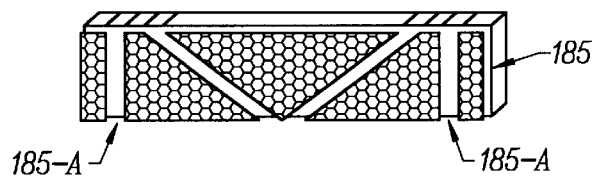
FIG. 5C depicts an "M"-shaped aperture mask, according to the present invention.

X-ray detectors 190 preferably are scintillant crystal units with photodiodes, and are known in the art. Although detectors 190 could have a simple rectangular shape, more useful data is obtained using "W"-shapes or "M"-shapes, similar to the apertures depicted in FIG. 5A or 5C. A detector so shaped may be effected by covering a rectangular detector with a mask 185 made from an X-ray opaque material, and having apertures 185-A and 185-A'. Preferably apertures such as shown in FIG. 5A or 5C will have edge-on cross-sections such as shown in FIG. 5E. As the projection of the beam-spot through one of the pinhole apertures 180-A moves across a mask 185, the X-rays that reach detector 190 behind that mask will produce detector output waveforms such as shown in FIG. 5B or 5D.

Consider, for example, a "W"-shaped aperture mask such as shown in FIG. 5A. For a beam-spot having an elongated shape, the beam-spot projection with X-rays 70' onto the mask 185 and detector 190 will also be elongated. In addition, the direction of motion of the beam-spot will be normal to its long axis such that direction of motion of its projection is substantially normal to the long axis of the projection. The mask preferably is oriented such that its central aperture is parallel to the long axis of the projection of the beam-spot.

As the projection of the beam-spot moves laterally across the mask, there will be two relatively long intervals of time during which some of the X-rays are detected through the respective inclined mask side-aperture channels 185-A'. The result will be two wide side pulses or lobes of intermediate signal amplitude. As the projection moves across the central mask aperture channel 185-A, there will be only a relatively short time interval during which any X-rays can pass through to the detector. Further, there will be an even shorter time interval during which substantially all of the X-rays can pass through, resulting in a central pulse of narrow width but large amplitude.

Figure 5B:
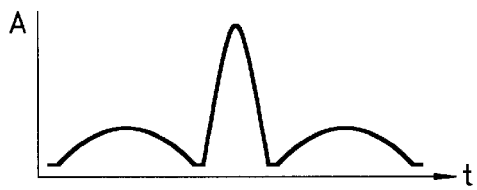
FIG. 5B depicts a shielded detector array output signal from a detector masked by the "W"-shaped aperture mask of FIG. 5A, produced by a phantom-like object comprising a shield with pinhole aperture, according to the present invention.
Figure 5D:
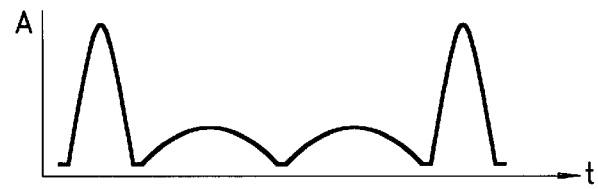
FIG. 5D depicts a shielded detector array output signal from a detector masked by the "M"-shaped aperture mask of FIG. 5C, produced by a phantom-like object comprising a shield with pinhole aperture, according to the present invention.
Figure 5E:
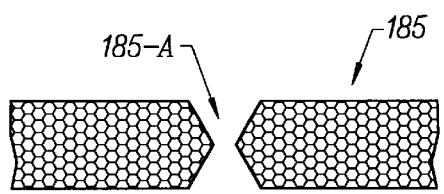
FIG. 5E is an edge-on view of a cross-section of an aperture in an aperture mask showing a preferred configuration, according to the present invention.

A shielded detector output waveform such as shown in FIG. 5B can provide a useful measure as to the position (e.g., as a function of timing and elliptical beam-spot radius), and shape of the electron beam-spot on target 50-C. The instant when the center of the central lobe is detected is a measure of the beam-spot timing, and the distance between the side-lobes is strongly dependent upon the beam-spot radius. Further, the shapes and relative sizes of the pulses provide information as to the beam-spot shape. For example, if the waveform shown in FIG. 5B were to favor one of the side-lobes, it would then be known in real-time that the projection of the beam-spot by X-rays 70' was more parallel to one of the side-aperture channels 185-A', rather than parallel to central aperture channel 185-A, as intended. Timing, beam-spot radius, ellipticity, and orientation characteristics may be extracted from the FIG. 5B waveform using techniques similar to those disclosed in the Rand-Plomgren patents. Beam-spot radius measurement determination will be changed somewhat as target movement and not just radius changes can alter the distance between lobes in detector output waveforms. Thus, extracting separate electron beam radius and target position measurements will involve comparing shielded detector output readings taken close in time from adjacent shielded detectors, such that the angle at which these shielded detectors see the electron beam-spot will differ.

FIG. 5C depicts an alternative configuration for the aperture mask, namely an "M"-shaped aperture mask that has two side aperture channels 185-A parallel to the long axis of the beam-spot projection, and two central inclined channels 185-A'. In the ideal case, the output from shielded detector array 190 would be similar to the detector waveform shown in FIG. 5D. The times at which the centers of each of the two large-amplitude side lobes are detected provide beam-spot timing information. The distance between the two lower amplitude central lobes will be strongly dependent upon the radius of the beam-spot, and the shapes and relative sizes of the pulses provide information as to beam-spot shape. An advantage of the "M" shaped aperture mask of FIG. 5B is that the shielded detector array output signal provides two primary lobes for measurement of beam-spot timing, as shown in FIG. 5D.

From the foregoing description it will be appreciated that by using a suitable shielded detector shape, obtained through the use of a slitted aperture mask disposed in front of these detectors, real-time information as to the timing, radius, and/or ellipticity characteristics of the electron beam-spot as it is scanned along the X-ray emitting target is provided. This information is obtained without interference with the normal operation of system 10 and is preferably fed back in real-time by circuitry 200, under control of computer system 150 to improve the quality of the electron beam-spot, and thus the quality of the imagery produced by system 10.

FIG. 5E is an edge-on view of a cross-section of an aperture in an aperture mask showing a preferred configuration. As noted, it is preferred that the aperture walls taper outward slightly, to improve detector sensitivity at oblique angles.

Figure 6:
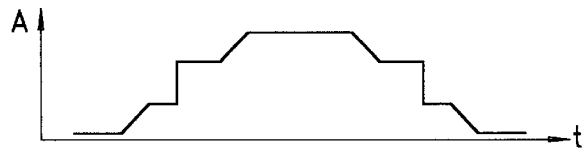
FIG. 6 depicts a shielded detector output signal from a detector masked by the "W"-shaped aperture mask of FIG. 5A, produced by a phantom-like object comprising a shield with slit aperture, with the slit direction parallel to the electron beam-spot path, according to the present invention.

The shielded detector array may use phantom-like objects other than exemplary shield 180 with its pinhole-shaped apertures 180-A. For example, FIG. 6 depicts the output signal from a detector 190 disposed behind a "W" aperture mask 185, such as depicted in FIG. 5A. In FIG. 6, shield 180 has a slit aperture that is in effect formed by a number of closely adjacent pinholes, with the slit direction parallel to the electron beam-spot path, according to the present invention. Note that the FIG. 6 waveform is essentially a time-integrated form of the "W"-mask waveform of FIG. 5B. A shield aperture that produces a shielded detector output signal such as shown in FIG. 6 advantageously can increase detection sensitivity at oblique angles, but at the cost of degraded signal-to-noise ratio.

Figure 7A:
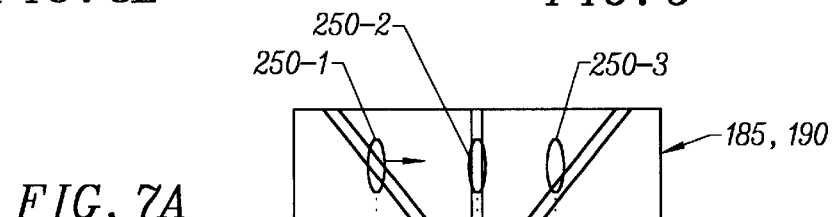
FIG. 7A depicts an "W"-shaped mask obscuring a detector, with a projection of an elliptical-shaped electron beam-spot shown at three times, according to the present invention.
Figure 7B:
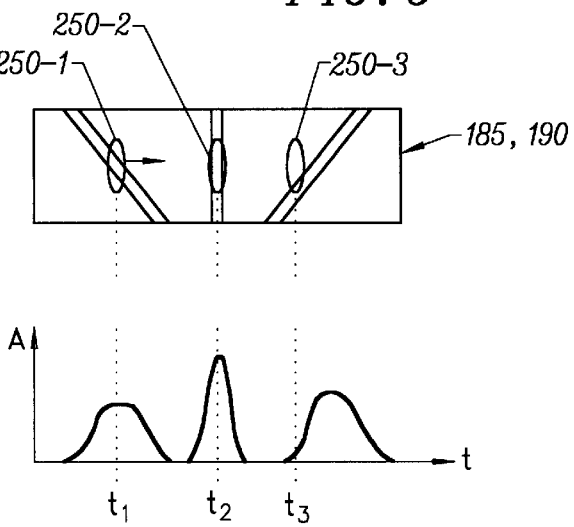
FIG. 7B shows detector amplitude output at three times showing the change in amplitude and width resulting from the relationship shown in FIG. 7A, according to the present invention.

FIG. 7A shows the relationship between an "W" mask 185, behind which is obscured detectors 90, with an X-ray projection 250 of the electron beam spot projected through a pin hole opening onto the masked detector. The projection is a narrow ellipse as the beam spot itself will be a narrow ellipse. The projection 250-1, 250-2, 250-3 is shown at three different times t1, t2, t3 as it moves left-to-right in FIG. 7A across mask 185. FIG. 7B shows amplitude A of the detector output signal. Note the large but narrow lobe corresponding to time t2 when the projection 250-2 is in alignment with the center channel of the mask, and the two smaller amplitude but wider lobes at times t1 and t3, when projection 250-1 is at the left diagonal mask channel, and later in time when the projection, denoted 250-3, is at the right diagonal mask channel.

In the various configurations of aperture masks that may be used or combined, preferably there will be more than one pinhole aperture 180-A per shielded detector 190. Preferably several timing measurements will be obtained per shielded detector, for example six to ten timing measurements. If thirty shielded detectors 190 are provided, and if the electron beam scan time was 100 ms, this configuration would provide two to three timing measurements per millisecond. As the electron beam-spot is scanned along the X-ray emitting target, the beam-spot will be seen almost simultaneously by at least three shielded detectors. Stated differently, at a given time the electron beam-spot will be projected onto three masked detectors at three different apparent angles. It will be appreciated that so-doing can provide further electron beam-spot characteristic information.

If desired, the masked detectors and associated apertures could be mounted within the pre-patient collimation system itself, but so-doing would dictate stringent dimensional constraints so as not to affect patient X-rays. So-doing would also make it more difficult to extract electron beam-spot shape from the shielded detector output signals due to the angle of X-rays to the target.

Referring back to FIG. 1, the output from the shielded detectors may be used to compensate for electron beam-spot error by modulating the timing clock used for digital-to-analog converters associated with beam magnets in beam optics assembly 40, thereby providing timing compensation. Alternatively, the shielded detector output data may instead be used to modulate the clock that synchronizes the DAS/detector data acquisition, thereby implementing an alternative method to compensate for detected timing errors. The shielded detector output data may be used to modulate offsets to beam magnets associated with the beam optics assembly 40, thereby compensating electron beam-spot timing and radius errors, and providing an opportunity to compensate for the shape of the beam-spot.

Initial placement of the masked detectors and the associated pinhole apertures may be determined from beam-spot position measurements made with prior art multi-pin phantom devices, which could provide a standard against which measurements made using the present invention could initially be calibrated.

Note that perceived target position can be measured by correlating the apparent "radius" measurements from adjacent masked detectors. If the position appears to have moved, the electron beam deflection path used for the next scan could be commanded by computer system 150, using information fedback from the shielded detector array, to adopt a more suitable path. During patient image reconstruction, the different radius information corresponding to the new deflection path could be used to improve quality of the image produced by system 10.

In addition to enabling real-time X-ray source position measurements during actual scans of a patient, the present invention provides a high measurement update rate to provide real-time feedback control of the X-ray source position. Further, the present invention advantageously can allow system 10 to function safely without the requirement for prior art "W"-type devices such as described in the Plomgren patent. In general, use of the present invention can improve performance of system 10, while relaxing magnetic field constraints and reducing system cost by allowing elimination of prior art devices that cannot detect real-time electron beam-spot characteristics.

Modifications and variations may be made to the disclosed embodiments without departing from the subject and spirit of the invention as defined by the following claims.

What is claimed is:

1. In a scanning electron beam computed tomographic system in which an electron beam is scanned across a target to emit a fan beam of X-rays some of which X-rays may pass through an area defined by a reconstruction radius and having an object therein to be detected by a detector array, a method of controlling at least one characteristic of a beam-spot formed by the scanned said electron beam upon said target, comprising the following steps:

(a) disposing a sub-collimation system to pass some X-rays emitted by said target when scanned by said electron beam, said sub-collimation system disposed to pass such X-rays as would not otherwise strike said object;

(b) detecting X-rays passing through said sub-collimation system at different angles such that a detection signal of said X-rays contains information associated with at least one characteristic of said beam-spot selected from a group consisting of (i) timing of said beam-spot along said target, (ii) apparent radius of said beam-spot along said target, and (iii) apparent shape of said beam spot along said target.

2. The method of claim 1, wherein step (a) includes providing an array of X-ray detectors masked by X-ray opaque masks defining at least one set "W"-shaped channels therein.

3. The method of claim 1, wherein step (a) includes providing an array of X-ray detectors masked by X-ray opaque masks defining at least one set of "M"-shaped channels therein.

4. The method of claim 1, wherein step (a) includes disposing a sheet of X-ray opaque material with a plurality of pinhole-shaped apertures formed therein between said target and a plurality of X-ray detectors disposed to detect at least some X-rays passing through at least some of said apertures.

5. The method of claim 4, wherein density of said apertures to said X-ray detectors is at least one to one.

6. The method of claim 4, wherein said sheet and said X-ray detectors are disposed coaxially about a Z-axis of said system.

7. The method of claim 1, further including:
   (c) feeding back an output signal obtained at step (b) to control scanning of said electron beam along said target.

8. The method of claim 1, further including:
   (c) feeding back an output signal obtained at step (b) to modulate deflection of said electron beam along said target.

9. The method of claim 1, further including:
   (c) feeding back an output signal obtained at step (b) to modulate timing of deflection of said electron beam along said target.

10. The method of claim 1, further including:
    (c) feeding back an output signal obtained at step (b) to modulate in real-time a beam deflection magnet in said system governing deflection of said electron beam along said target.

11. The method of claim 1, further including:
    (c) feeding back an output signal obtained at step (b) to modulate in real-time a DAS clock to compensate for timing error in deflection of said electron beam along said target.

12. For use with a scanning electron beam computed tomographic system in which an electron beam is scanned across a target to emit a fan beam of X-rays some of which X-rays may pass through an area defined by a reconstruction radius and having an object therein to be detected by a detector array, a system to control at least one characteristic of a beam-spot formed by the scanned said electron beam upon said target, the system comprising:
    a sub-collimation system disposed in said computed tomographic system to pass some X-rays emitted by said target when scanned by said electron beam, said sub-collimation system disposed to pass such X-rays as would not otherwise strike said object; and
    a detection system to detect X-rays passing through said sub-collimation system at different angles such that a detection signal of said X-rays contains information associated with at least one characteristic of said beam-spot selected from a group consisting of (i) timing of said beam-spot along said target, (ii) apparent radius of said beam-spot along said target, and (iii) apparent shape of said beam spot along said target.

13. The system of claim 12, wherein said sub-collimation system includes an array of X-ray detectors and X-ray opaque masks defining at least one set of "W"-shaped channels therein, said X-ray detectors being masked by said X-ray opaque masks.

14. The system of claim 12, wherein said sub-collimation system includes a detector array and X-ray opaque masks defining at least one set of "M"-shaped channels therein, said X-ray detectors being masked by said X-ray opaque masks.

15. The system of claim 12, wherein said sub-collimation system includes a sheet of X-ray opaque material with a plurality of pinhole-shaped apertures formed therein disposed between said target and a plurality of X-ray detectors disposed to detect at least some X-rays passing through at least some of said apertures;
    wherein said sheet and said X-ray detectors are disposed coaxially about a Z-axis of said system.

16. The system of claim 12, wherein density of said apertures to said X-ray detectors is at least three to one.

17. The system of claim 12, further including:
    a circuit to feed back an output signal from said detection system to control scanning of said electron beam along said target.

18. The system of claim 12, wherein said circuit feeds back an output signal obtained from said detection system to modulate deflection of said electron beam along said target.

19. The system of claim 12, wherein said circuit feeds back an output signal obtained from said detection system to modulate timing of deflection of said electron beam along said target.

20. The system of claim 12, wherein said circuit feeds back an output signal obtained from said detection system to modulate in real-time a beam deflection magnet in said system governing deflection of said electron beam along said target.

21. The system of claim 12, wherein said circuit feeds back an output signal obtained from said detection system to modulate in real-time a DAS clock to compensate for timing error in deflection of said electron beam along said target.

* * * * *